(12) United States Patent
Kaminaga et al.

(10) Patent No.: US 10,361,102 B2
(45) Date of Patent: Jul. 23, 2019

(54) CUTTING APPARATUS

(71) Applicant: DISCO CORPORATION, Tokyo (JP)

(72) Inventors: Takuya Kaminaga, Tokyo (JP); Tomoaki Sugiyama, Tokyo (JP); Saki Miyakawa, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 0 days.

(21) Appl. No.: 15/875,242

(22) Filed: Jan. 19, 2018

(65) Prior Publication Data

US 2018/0211851 A1 Jul. 26, 2018

(30) Foreign Application Priority Data

Jan. 20, 2017 (JP) ................ 2017-008473

(51) Int. Cl.
| | |
|---|---|
| *H01L 21/67* | (2006.01) |
| *H01L 21/683* | (2006.01) |
| *G06F 9/48* | (2006.01) |
| *B26D 5/00* | (2006.01) |
| *G01N 29/36* | (2006.01) |
| *B26D 7/12* | (2006.01) |
| *G01N 29/14* | (2006.01) |
| *G01N 29/42* | (2006.01) |

(52) U.S. Cl.
CPC ........ *H01L 21/67092* (2013.01); *B26D 5/005* (2013.01); *B26D 7/12* (2013.01); *G01N 29/14* (2013.01); *G01N 29/36* (2013.01); *G01N 29/42* (2013.01); *G06F 9/485* (2013.01); *H01L 21/67253* (2013.01); *H01L 21/683* (2013.01); *H01L 2221/683* (2013.01)

(58) Field of Classification Search
CPC ........ H01L 21/67092; H01L 21/67253; B26D 5/005; B26D 7/12; G01N 29/14; G01N 29/36; G01N 29/42; G06F 9/485
See application file for complete search history.

(56) References Cited

U.S. PATENT DOCUMENTS

| | | | | |
|---|---|---|---|---|
| 6,413,789 | B2 * | 7/2002 | Ostapenko | ........ H01L 21/67253 257/E21.53 |
| 7,377,168 | B2 * | 5/2008 | Liu | ...................... G01N 27/025 73/579 |

(Continued)

FOREIGN PATENT DOCUMENTS

JP 2000-049120 A 2/2000

*Primary Examiner* — Omar Flores Sanchez
(74) *Attorney, Agent, or Firm* — Greer Burns & Crain, Ltd.

(57) ABSTRACT

A cutting apparatus includes a cutting unit including a cutting blade that has a cutting edge for cutting a dresser board. An elastic wave detection sensor is disposed in the cutting unit, for detecting an elastic wave produced when the dresser board is cut. The elastic wave detection sensor produces an output signal representing the detected elastic wave when the cutting blade cuts the dresser board and is dressed thereby, the output signal being variable as the cutting blade is progressively dressed by the dresser board. A control unit stores in advance, as a threshold value, the value of the output signal when the dressing of the cutting blade is completed. The control unit stops cutting the dresser board with the cutting blade and finishes the dressing of the cutting blade when the output signal produced by the elastic wave detection sensor reaches the threshold value.

1 Claim, 4 Drawing Sheets

(56) References Cited

U.S. PATENT DOCUMENTS

2001/0046720 A1* 11/2001 Ostapenko ........ H01L 21/67253
438/14
2013/0166214 A1* 6/2013 Bellin .................... G01N 29/14
702/9
2017/0036261 A1* 2/2017 Iwakuro ................. B21D 55/00

* cited by examiner

CUTTING APPARATUS

BACKGROUND OF THE INVENTION

Field of the Invention

The present invention relates to a cutting apparatus for cutting a plate-shaped workpiece such as a semiconductor wafer with a cutting blade.

Description of the Related Art

Heretofore, a cutting apparatus having a rotatable circular cutting blade mounted on the end of a spindle has been used as an apparatus for dividing a plate-shaped workpiece such as a semiconductor wafer, a glass substrate, or a resin substrate into device chips. The cutting blade cuts the plate-shaped workpiece while being rotated at a high speed by the spindle. One problem with the cutting blade is that while in use it tends to be loaded with cutting dust produced from the workpiece being cut and deposited on the cutting edge thereof, resulting in a reduction in its cutting capability. According to a solution to the problem, a dressing process is performed to remove the loading material from the cutting blade by having it cut into a dresser board during an interval between cutting sessions (for example, see Japanese Patent Laid-open No. 2000-49120).

SUMMARY OF THE INVENTION

Japanese Patent Laid-open No. 2000-49120 discloses a dressing process for dressing the cutting edge of a cutting blade. The disclosed dressing process, however, is ambiguous about how much material of the cutting blade is to be removed by dressing before its cutting capability is improved or recovered. At present, the operator empirically determines an amount of cutting blade material to be removed by dressing, though the empirical practice leads to frequent instances where the operator removes an unnecessary undue amount of cutting blade material by dressing. As a result, the dressing process is apt to be time-consuming and the life cycle of each cutting blade prior to replacement tends to be short.

It is an object of the present invention to provide a cutting apparatus having a cutting blade whose material is prevented from being unduly removed by dressing.

In accordance with an aspect of the present invention, there is provided a cutting apparatus including a holding table for holding a plate-shaped workpiece, a cutting unit including a cutting blade that has a cutting edge for cutting the plate-shaped workpiece held on the holding table, a cutting-feed unit for cutting-feeding the holding table and the cutting unit relatively to each other in cutting-feed directions, an indexing-feed unit for indexing-feeding the holding table and the cutting unit relatively to each other in indexing-feed directions perpendicular to the cutting-feed directions, an elastic wave detection sensor disposed in either one of the cutting unit and the holding table, for detecting an elastic wave produced when the plate-shaped workpiece held on the holding table is cut by the cutting blade, and a control unit for controlling the cutting-feed unit and the indexing-feed unit. The elastic wave detection sensor produces an output signal representing the detected elastic wave when the cutting blade cuts a dresser board held on the holding table and is dressed thereby, the output signal being variable as the cutting blade is progressively dressed by the dresser board, and the control unit includes a storage unit that stores in advance, as a threshold value, the value of the output signal produced by the elastic wave detection sensor when the dressing of the cutting blade is completed, and the control unit stops cutting the dresser board with the cutting blade and finishes the dressing of the cutting blade on the dresser board held on the holding table when the output signal produced by the elastic wave detection sensor reaches the threshold value stored in the storage unit.

With the above arrangement, the elastic wave produced when the cutting blade is dressed by the dresser board is detected, and the dressing of the cutting blade is stopped when the detected elastic wave reaches the threshold value. Therefore, the dressing of the cutting blade is finished at an appropriate timing. Consequently, the cutting blade can be dressed without an undue amount of cutting blade material being removed and can be dressed within a reduced period of time. In addition, a cycle for replacing the cutting blade is increased. According to the present invention, therefore, as the elastic wave produced when the cutting blade is dressed is detected, and the dressing of the cutting blade is finished at an appropriate timing on the basis of the detected elastic wave, an undue amount of cutting blade material is prevented from being removed from the cutting blade due to the dressing thereof.

The above and other objects, features and advantages of the present invention and the manner of realizing them will become more apparent, and the invention itself will best be understood from a study of the following description and appended claim with reference to the attached drawings showing a preferred embodiment of the invention.

DETAILED DESCRIPTION OF THE PREFERRED EMBODIMENT

Figure 1:
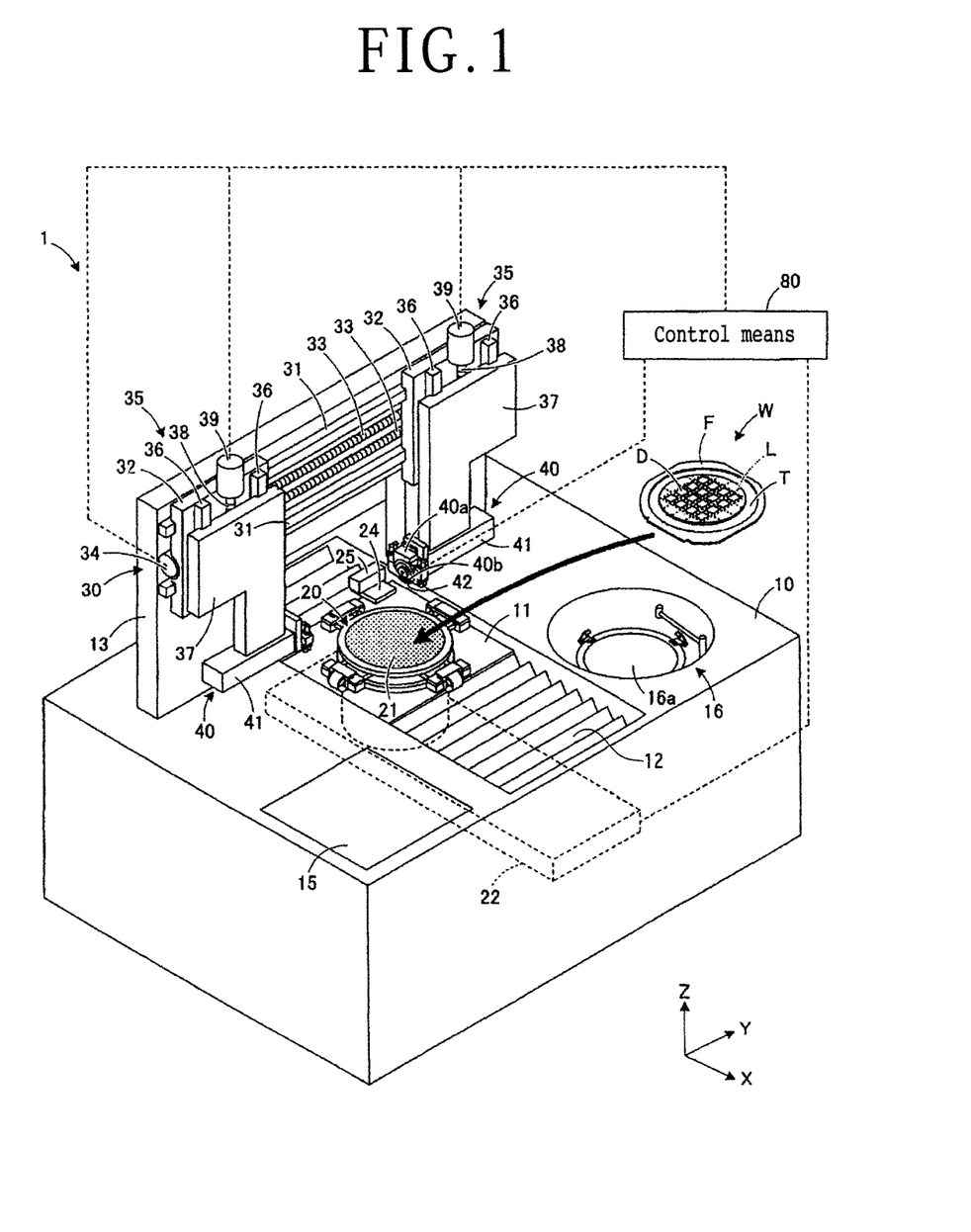
FIG. 1 is a perspective view of a cutting apparatus according to an embodiment of the present invention.

A cutting apparatus according to an embodiment of the present invention will be described below with reference to the accompanying drawings. FIG. 1 depicts in perspective a cutting apparatus according to an embodiment of the present invention. The cutting apparatus is not limited to the details depicted in FIG. 1, but may be constructed otherwise as long as it has an arrangement for detecting an elastic wave generated when a cutting blade is dressed. In FIG. 1, certain parts are omitted from illustration for the sake of brevity, but the cutting apparatus should be provided with those features that ordinary cutting apparatus have as essential features.

As depicted in FIG. 1, the cutting apparatus, generally denoted by 1, according to the present embodiment includes a pair of cutting means (cutting unit) 40 each having a cutting blade 42 and a chuck table 20 for holding a workpiece W thereon. The cutting blade 42 and the chuck table 20 are moved relatively to each other while the cutting blade 42 cuts the workpiece W. The workpiece W has a face side demarcated into a plurality of areas by a grid of projected dicing lines L, with devices D formed in the respective areas. The workpiece W is affixed to a dicing tape T within a ring frame F that is also affixed to the dicing tape T. The workpiece W that is supported on the ring frame F by the dicing tape T is introduced into the cutting apparatus 1.

The workpiece W may be of any material insofar as it can be cut by the cutting apparatus 1. The workpiece W may include a semiconductor wafer such as a semiconductor substrate made of silicon or gallium arsenide on which semiconductor devices such as integrated circuits (ICs) or large-scale integration (LSI) formed. Alternatively, the workpiece W may include an optical device wafer such as a substrate made of an inorganic material such as sapphire or silicon carbide on which optical devices such as LEDs formed. Further alternatively, the workpiece W may include a packaged substrate such as a chip size package (CSP), a printed-circuit board, a metal substrate or an adhesive tape such as a die attach film (DAF) to be affixed to the reverse side of a wafer.

The cutting apparatus 1 also includes a base 10 with an opening defined in its upper surface and extending in X-axis directions. The opening is covered with a movable plate 11 and a bellows-like water resistant cover 12 that are movable with the chuck table 20. The chuck table 20 has a holding surface 21 made of a porous material as its upper surface for holding the workpiece W under suction thereon. The holding surface 21 is connected to a suction source, not depicted, through a channel defined in the chuck table 20. The workpiece W is held under suction on the holding surface 21 by a negative pressure generated by the suction source and acting on the holding surface 21. The water resistant cover 12 is disposed over ball-screw-type cutting-feed means (cutting-feed unit) 22 housed in the base 10, for cutting-feeding the chuck table 20 in the X-axis directions. The ball-screw-type cutting-feed means 22 cutting-feeds the chuck table 20 and the cutting means 40 relatively to each other in cutting-feed directions which are represented by the X-axis directions.

A sub-chuck table (holding table) 24 is disposed on the movable plate 11 in the vicinity of the chuck table 20. The sub-chuck table 24 holds under suction thereon a rectangular dresser board (plate-shaped workpiece) 25 used to dress the cutting blade 42.

Elevator means 15 and a spinner cleaning mechanism 16 are mounted on the base 10 one on each side of the opening. The spinner cleaning mechanism 16 has a spinner table 16a for holding the workpiece W thereon. The spinner cleaning mechanism 16 ejects cleaning water to the spinner table 16a while in rotation to clean the workpiece W held thereon, and thereafter ejects drying air to the workpiece W, thereby drying the workpiece W.

Indexing-feed means (indexing-feed unit) 30 for moving the cutting means 40 in Y-axis directions is mounted on a portal-shaped upstanding wall 13 that is disposed on an upper surface of the base 10. The indexing-feed means 30 moves the cutting means 40 in the Y-axis directions to indexing-feed the cutting means 40 and the chuck table 20 relatively to each other. The indexing-feed directions in which the cutting means 40 and the chuck table 20 are indexing-fed relatively to each other are represented by the Y-axis directions which are perpendicular to the cutting-feed direction represented by the X-axis directions. The indexing-feed means 30 has a pair of guide rails 31 disposed on a front surface of the upstanding wall 13 and lying parallel to the Y-axis directions, and a pair of Y-axis tables 32 slidably mounted on the guide rails 31. The upstanding wall 13 supports thereon respective incising-feed means (incising-feed units) 35 for incising-feeding the respective cutting means 40 in Z-axis directions. Each of the incising-feed means 35 has a pair of guide rails 36 disposed on one of the Y-axis tables 32 and lying parallel to the Z-axis directions, and a Z-axis table 37 slidably mounted on the guide rails 36.

The cutting means 40 for cutting the workpiece W are mounted on respective lower portions of the Z-axis tables 37. Nuts are disposed on respective rear surfaces of the Y-axis tables 32 and the Z-axis tables 37, and ball screws 33 and 38 are threaded through the nuts. Drive motors 34 and 39 are coupled to respective ends of the ball screws 33 on the Y-axis tables 32 and the ball screws 38 on the Z-axis tables 37. When the drive motors 34 and 39 are energized, they rotate the respective ball screws 33 and 38 about their own axes, moving the cutting means 40 along the guide rails 31 in one of the Y-axis directions and also moving the cutting means 40 along the guide rails 36 in one of the Z-axis directions. The drive motors 34 and 39 are controlled by control means (control unit) 80 to be described later.

The cutting-feed means 22, the indexing-feed means 30, and the incising-feed means 35 move the cutting means 40 relatively to the chuck table 20 in the X-, Y-, and Z-axis directions and also move the cutting means 40 relatively to the sub-chuck table 25 in the X-, Y-, and Z-axis directions.

In each of the cutting means 40, the cutting blade 42 is mounted on the distal end of a spindle, not depicted, projecting from a spindle housing 41. The cutting blade 42 is made of abrasive grains of diamond or the like that are bound (sintered) into a disk shape by a bonding agent. Details of the cutting means 40 will be described later.

The cutting apparatus further includes the control means 80 that integrally controls various components of the cutting apparatus 1 including at least the cutting-feed means 22, the indexing-feed means 30, and the incising-feed means 35. The control means 80 includes a processor for performing various processing processes, a memory, etc. The memory includes one or more storage mediums including a read only memory (ROM), a random access memory (RAM), etc.

A process of cutting the workpiece W using the cutting apparatus 1 will be described below. First, the workpiece W affixed to the ring frame F by the dicing tape T, which are handled as a unit, is delivered by delivering means, not depicted, to the chuck table 20 and held under suction on the chuck table 20. Then, the workpiece W is directionally aligned, after which the chuck table 20 is moved in one of the X-axis directions to position the workpiece W beneath the cutting means 40 closely thereto. The indexing-feed means 30 moves the cutting means 40 in one of the Y-axis directions into alignment with projected dicing lines on the workpiece W.

Thereafter, the cutting means 40 are lowered to a position in the Z-axis directions which corresponds to the depth to which the workpiece W is to be incised. After the cutting means 40 are thus positioned, the chuck table 20 is moved in one of the X-axis directions with respect to the cutting blades 42 that are being rotated at a high speed, forming grooves in the workpiece W along projected dicing lines L thereon. Each time one groove is formed in the workpiece W by each of the cutting means 40, the cutting means 40 is moved in one of the Y-axis directions by a distance corresponding to an interval or pitch between two projected dicing lines L in the Y-axis directions. Then, the chuck table 20 is moved again with respect to the cutting blades 42 to repeat the above cutting cycle. In this manner, grooves are successively cut in the workpiece W. After grooves have been cut in the workpiece W along the projected dicing lines L parallel to the X-axis directions, the chuck table 20 is turned 90° by a θ table, not depicted. The above cutting cycle is repeated to cut grooves in the workpiece W perpendicularly to the previously formed grooves. In this manner, the grooves are cut in the workpiece W along all the projected dicing lines L thereon, thereby cutting the workpiece W in a grid pattern.

When the above cutting cycle is repeated, the cutting blade 42 of each cutting means 40 tends to be loaded with cutting dust produced from the workpiece W and deposited on the cutting edge thereof, resulting in a reduction in its cutting capability. Therefore, the cutting blade 42 is periodically dressed. For dressing the cutting blade 42, the dresser board 25 is placed and held in position on the sub-chuck table 24. Then, in a manner similar to cutting the workpiece W, the cutting means 40 is moved relatively to the sub-chuck table 24, causing the cutting blade 42 to cut into the dresser board 25 to a predetermined depth. The cutting edge, denoted by 58 (see FIG. 3), of the cutting blade 42 is now dressed, exposing abrasive grains on the cutting edge 58 and creating a new cutting edge.

Figure 2:
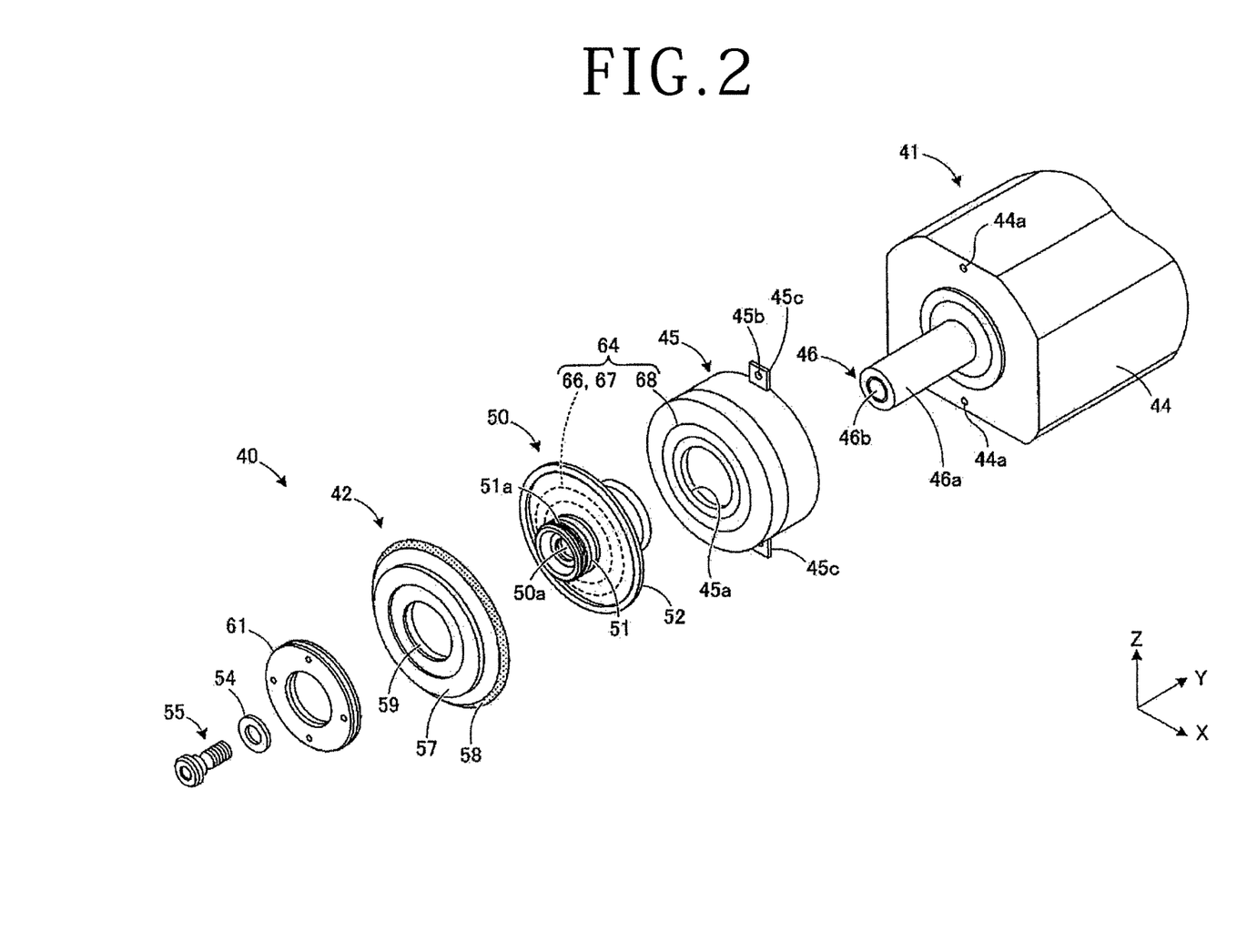
FIG. 2 is an exploded perspective view of cutting means according to the embodiment.
Figure 3:
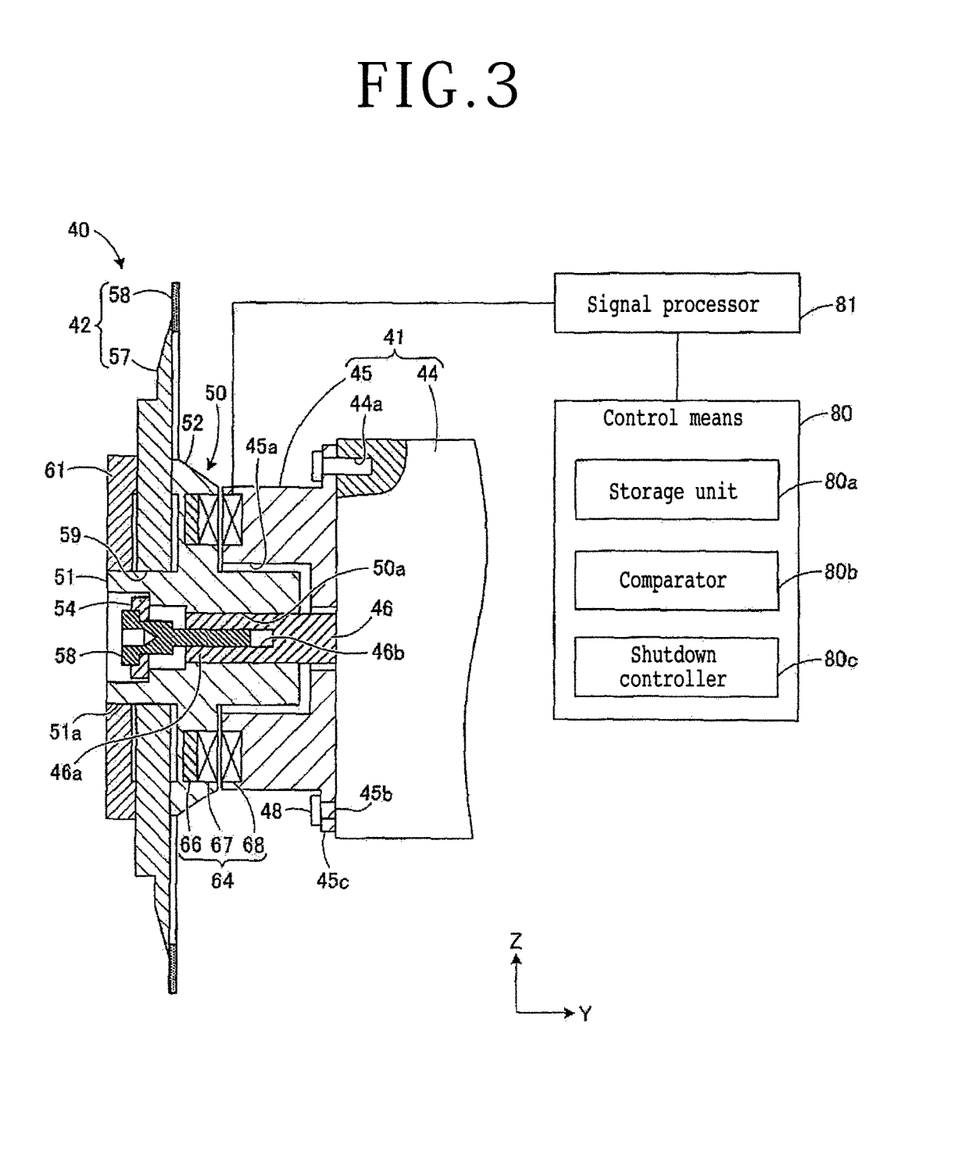
FIG. 3 is a schematic cross-sectional view of the cutting means according to the embodiment, with control means and a signal processor being illustrated in block form.

One of the cutting means 40 according to the present embodiment will be described below with reference to FIGS. 2 and 3. Since the other cutting means 40 is structurally identical, only one of the cutting means 40 will be described below. FIG. 2 depicts in exploded perspective the cutting means 40 according to the embodiment, and FIG. 3 depicts in schematic cross section the cutting means 40 according to the embodiment, with control means and a signal processor being illustrated in block form. In FIGS. 2 and 3, a wheel cover that covers the outer periphery of the cutting blade is omitted from illustration for the sake of brevity. The cutting means may be of any structure as long as it allows the cutting blade according to the present embodiment to be mounted in place, and hence is not limited to the structural details depicted in FIGS. 2 and 3.

As depicted in FIGS. 2 and 3, the cutting means 40 includes the spindle housing 41 that is mounted on the lower portion of the Z-axis table 37 (see FIG. 1). The spindle housing 41 includes a housing body 44 and a hollow cylindrical housing cover 45 mounted on an end of the housing body 44.

The housing body 44 houses therein a spindle 46 that is rotatable about its own axis extending in the Y-axis directions. The spindle 46 includes an air spindle, for example, and is floatingly supported in the housing body 44 by a compressed air layer. The spindle 46 has a distal end portion 46a projecting from an end wall of the housing body 44.

The housing cover 45 has a circular opening 45a defined centrally therein. The housing cover 45 has a pair of diametrically opposite engaging portions 45c with respective holes 45b defined therein, on an end thereof which faces the housing body 44. The housing cover 45 is securely fastened to the housing body 44 by screws 48 (not depicted in FIG. 2; see FIG. 3) that are threaded through internally threaded holes 45b in the engaging portions 45c into internally threaded holes 44a in the housing body 44, with the one end of the spindle 46 extending through the opening 45a.

The spindle 46 has an internally threaded hole 46b that is defined in the distal end portion 46a thereof and open at the end face of the distal end portion 46a. A support flange 50 is securely mounted on the distal end portion 46a of the spindle 46. The support flange 50 has a hollow cylindrical boss 51 and a flanged mount 52 extending radially outwardly from the peripheral surface of the boss 51.

The support flange 50 has an opening 50a defined axially through the boss 51. The distal end portion 46a of the spindle 46 is fitted into the opening 50a from behind the flange support 50, i.e., from the spindle housing 45 side. Then, a washer 54 is placed in the opening 54a, and a fastening bolt 55 is threaded through the washer 54 into the internally threaded hole 46b, thereby fastening the support flange 50 to the spindle 46.

The cutting blade 42 is a hub blade including a hub base 57 substantially in the form of a centrally open disk and an annular cutting edge 58 disposed on the outer peripheral edge of the hub base 57. The hub base 57 has an insertion hole 59 defined centrally therein through which the boss 51 of the support flange 50 is inserted. The cutting edge 58 is made of abrasive grains of diamond, cubic boron nitride (CBN), or the like mixed with a bonding agent (bonding material) such as metal or resin and shaped to a predetermined thickness. Alternatively, the cutting blade 42 may be a washer blade including a cutting edge only.

When the boss 51 is inserted into the insertion hole 59 in the hub base 57, the boss 51 has a portion projecting from the hub base 57. The projecting portion of the boss 51 has an externally threaded outer circumferential surface 51a, and an annular fastening nut 61 is threaded and tightened over the externally threaded outer circumferential surface 51a, thereby fixing the cutting blade 42 to the support flange 50. In this manner, the support flange 50 is mounted on the distal end portion 46a of the spindle 46, and the cutting blade 42 is mounted on the support flange 50.

The cutting means 40 includes an elastic wave detection sensor 64 for detecting an elastic wave produced when the cutting blade 42 cuts the dresser board 25 (see FIG. 1) held on the sub-chuck table 24.

The elastic wave detection sensor 64 includes an acoustic emission (AE) sensor having a function to detect an elastic wave, for example. Specifically, the elastic wave detection sensor 64 includes an ultrasonic oscillator 66 fixedly disposed in the support flange 50. The ultrasonic oscillator 66 is made of barium titanate ($BaTiO_3$), lead zirconate titanate ($Pb(Zi,Ti)O_3$), lithium niobate ($LiNbO_3$), or lithium tantalate ($LiTaO_3$) and serves to transform vibrations of the cutting blade 42 into a voltage (oscillating signal). The ultrasonic oscillator 66 resonates with vibrations at a predetermined frequency, and may have a vibration frequency determined that it can detect as the elastic wave detection sensor 64 in accordance with the resonant frequency. According to an alternative arrangement, a plurality of support flanges 50 may house therein respective ultrasonic oscillators 66 having different resonant frequencies, and one of the support flanges 50 may be selected and used depending on processing conditions for the cutting apparatus 1.

The elastic wave detection sensor 64 includes first coil means 67 disposed in the support flange 50 and connected to the ultrasonic oscillator 66, and second coil means 68 disposed in the housing cover 45 and facing the first coil 67 across a gap. The first coil means 67 and the second coil means 68 may include an annular coil of a conductive wire, for example.

The first coil means 67 and the second coil means 68 are magnetically coupled to each other. A voltage generated by the ultrasonic oscillator 66 is transmitted from the first coil means 67 to the second coil means 68 by way of mutual induction between the first coil means 67 and the second coil means 68.

As depicted in FIG. 3, the control means 80 is electrically connected to the second coil means 68 through a signal processor 81. The signal processor 81 includes an amplifier and other circuitry for converting an output signal from the acoustic wave detection sensor 64 into an output voltage. Therefore, the output signal from the acoustic wave detection sensor 64 is supplied as a converted output signal (output voltage or the like) from the signal processor 81 to the control means 80.

The control means 80 includes a storage unit 80a, which includes the memory referred to above, storing a threshold value to be compared with the output signal from the acoustic wave detection sensor 64. The control means 80 also includes a comparator 80b and a shutdown controller 80c. The comparator 80b compares the output signal from the acoustic wave detection sensor 64 with the threshold value stored in the storage unit 80a, and determines whether the output signal has reached the threshold value or not. Depending on the result of comparison from the comparator 80b, the shutdown controller 80c stops operating the feed means 22, 30, and 35 immediately or after they have performed given operations, thereby finishing the dressing process on the cutting blade 42.

When the cutting edge 58 of the rotating cutting blade 42 contacts the upper surface of the dresser board 25 (see FIG. 1) for dressing the cutting blade 42 on the dresser board 25, the cutting blade 42 produces an elastic wave. The produced elastic wave is commensurate with the surface roughness of the cutting edge 58 at the time the cutting edge 58 contacts the dresser board 25 and is cutting-fed on the dresser board 25. The elastic wave is propagated to the elastic wave detection sensor 64 positioned near the cutting blade 42, and the elastic wave detection sensor 64 detects the propagated elastic wave and outputs an AE value dependent on the detected elastic wave as its output signal. As the dressing of the cutting blade 42 progresses, the surface roughness of the cutting edge 58 decreases, and the AE value output from the elastic wave detection sensor 64 also varies according to the decrease in the surface roughness of the cutting edge 58.

Figure 4:
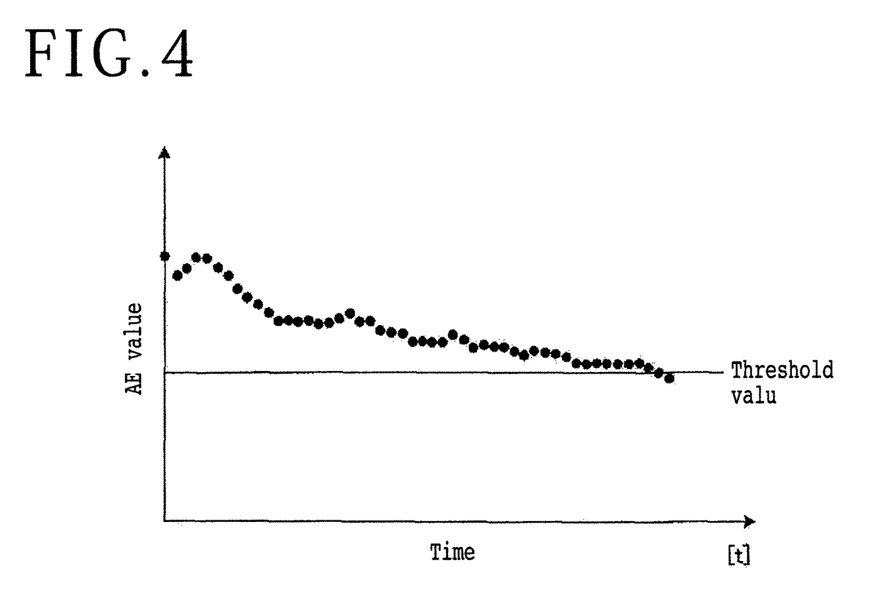
FIG. 4 is a graph depicting detection results of an elastic wave detection sensor.

FIG. 4 is a graph depicting detection results of the elastic wave detection sensor 64. The vertical axis of the graph represents the AE values output from the elastic wave detection sensor 64, and the horizontal axis time. The graph illustrates the detection results of the elastic wave detection sensor 64 from the time when the cutting blade 42 is loaded with cutting dust until the time when the dressing of the cutting blade 42 is completed. As depicted in FIG. 4, when the cutting blade 42 is loaded with cutting dust and hence the cutting edge 58 is coarse, the impact energy generated by the rotating cutting edge 58 upon contact with the dresser board 25 varies to a large extent, resulting in an increase in the AE value as the output signal from the elastic wave detection sensor 64, unlike when the dressing of the cutting blade 42 is completed. As the cutting blade 42 is progressively dressed to sharpen the cutting edge 58, the AE value output from the elastic wave detection sensor 64 varies so as to become relatively smaller. The storage unit 80a of the control means 80 has stored, as the threshold value, an AE value output from the elastic wave detection sensor 64 at the time the dressing of the cutting blade 42 is completed. The threshold value can be determined by dressing the cutting blade 42 depending on the type of the cutting blade 42, the type of the dresser board 25, processing conditions, etc. and detecting an actual generated elastic wave with the elastic wave detection sensor 64 at the time the dressing of the cutting blade 42 is completed. The threshold value thus determined may be multiplied by a predetermined coefficient, providing a new threshold range insofar as it is allowable for a dressed finish in the dressing process.

While the cutting blade 42 is being dressed, the comparator 80b of the control means 80 compares the threshold value stored in the storage unit 80a and the AE value output from the elastic wave detection sensor 64 and delivered via the signal processor 81 with each other, and determines whether the AE value from the elastic wave detection sensor 64 has reached the threshold value or not, i.e., whether the AE value is smaller than the threshold value or not. If the comparator 80b decides that the AE value is smaller than the threshold value, then the shutdown controller 80c stops operating the feed means 22, 30, and 35 immediately or after they have performed given operations, thereby stopping cutting the dresser board 25 on the cutting blade 42 and hence finishing the dressing process on the cutting blade 42. After the dressing process is finished, the cutting process on the workpiece W is started or resumed.

According to a conventional dressing process, it has been the practice to dress the cutting blade in an empirically preset number of dressing processes, rather than stopping a dressing process depending on the detection result of an elastic wave produced by the cutting blade according to the present embodiment. Therefore, the amount of cutting blade material to be removed by dressing is determined beforehand depending on the number of dressing processes to be performed on the cutting blade.

According to the present embodiment, however, the cutting apparatus 1 detects an elastic wave produced when the cutting edge 58 of the cutting blade 42 is dressed by the dresser board 25 and compares the detected elastic wave with the threshold value based on an elastic wave detected when the dressing of a cutting blade is completed. Therefore, when the detected elastic wave reaches the threshold value, it can be determined that the loading on the cutting blade 58 is eliminated and the surface roughness of the cutting edge 58 is normal. Consequently, it is not necessary to perform a preset number of dressing processes on the cutting blade 42 as is the case with the conventional dressing practice, but the dressing of the cutting blade 42 can be finished in a shorter period of time than with the conventional dressing practice, and the removal of an undue amount of cutting blade material due to dressing is prevented. As a result, the accuracy of the dressing process is increased, and at the same time the dressing process is performed in a shorter period of time, and the same cutting blade 42 can be used over a longer period of time.

The elastic wave detection sensor 64 may be installed in another position in the cutting means 40, e.g., in a wheel cover 40a (see FIG. 1) that covers the outer periphery of the cutting blade 42, or in a nozzle (silicone nozzle) 40b (see FIG. 1) for supplying cutting water.

Figure 5:
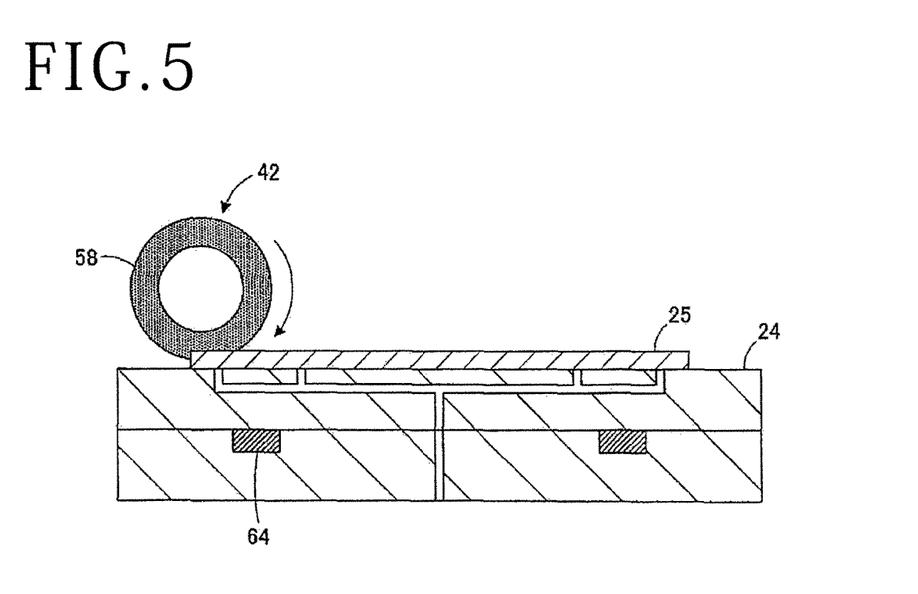
FIG. 5 is a schematic cross-sectional view of a dresser board and a sub-chuck table according to a modification.

The elastic wave detection sensor 64 may be disposed in either one of the cutting means 40 and the sub-chuck table 24. According to a modification depicted in FIG. 5, for example, the elastic wave detection sensor 64 may be embedded in the sub-chuck table 24. In the modification depicted in FIG. 5, the elastic wave detection sensor 64 may be of an annular shape as viewed in plan or may be in the form of separate sensors angularly spaced at predetermined angular intervals in peripheral directions of the dresser board 25. If the elastic wave detection sensor 64 is thus positioned in the sub-chuck table 24 according to the modification, the first and second coil means 67 and 68 according to the above embodiment may be dispensed with.

The control means 80 may perform a Fourier transform on the waveform of the output voltage from the elastic wave detection sensor 64 to detect the elastic wave produced by the cutting blade 42 as separate major frequency components. The Fourier analysis makes it possible to recognize an oscillation mode (oscillating component) at frequencies not seen in a waveform representing the cutting edge 58 not loaded, from a waveform representing the loaded cutting edge 58, thereby allowing the control means 80 to determine whether the surface roughness of the cutting edge 58 is normal or not.

Though the cutting apparatus 1 for cutting or dividing the workpiece W has been illustrated in the present embodiment, the cutting apparatus according to the present invention may be used to trim the edge of the workpiece W, for example.

The present invention is not limited to the embodiment and modification described above, but many changes, replacements, and modifications may be made without departing from the scope of the present invention. Furthermore, the present invention may be reduced to practice according to other techniques, processes, schemes, plans, or arrangements insofar as they are capable of implementing the principles of the present invention owing to technological advances or derivations. Therefore, the appended scope of the claim should be interpreted as covering all the embodiments falling within the range of the technical idea of the present invention.

As described above, the present invention offers advantages in that an undue amount of cutting blade material is prevented from being removed when the cutting blade is dressed, and is particularly useful as a cutting apparatus in which the cutting edge is to be dressed a plurality of times.

The present invention is not limited to the details of the above described preferred embodiment. The scope of the invention is defined by the appended claim and all changes and modifications as fall within the equivalence of the scope of the claim are therefore to be embraced by the invention.

What is claimed is:

1. A cutting apparatus comprising:
a holding table for holding a plate-shaped workpiece;
a cutting unit including a cutting blade that has a cutting edge for cutting the plate-shaped workpiece held on said holding table;
a cutting-feed unit for cutting-feeding said holding table and said cutting unit relatively to each other in cutting-feed directions;
an indexing-feed unit for indexing-feeding said holding table and said cutting unit relatively to each other in indexing-feed directions perpendicular to said cutting-feed directions;
an elastic wave detection sensor disposed in either one of said cutting unit and said holding table, for detecting an elastic wave produced when the plate-shaped workpiece held on said holding table is cut by said cutting blade; and
a control unit for controlling said cutting-feed unit and said indexing-feed unit, wherein
said elastic wave detection sensor produces an output signal representing the detected elastic wave when said cutting blade cuts a dresser board held on said holding table and is dressed thereby, said output signal being variable as said cutting blade is progressively dressed by said dresser board, and said control unit includes a storage unit that stores in advance, a threshold value, which is a previously determined value corresponding to an output signal produced by said elastic wave detection sensor when the dressing of said cutting blade is completed, and
said control unit stops cutting said dresser board with said cutting blade and finishes the dressing of said cutting blade on the dresser board held on said holding table when the output signal produced by said elastic wave detection sensor reaches the threshold value stored in said storage unit.

* * * * *